(12) United States Patent
Shen et al.

(10) Patent No.: US 10,072,125 B2
(45) Date of Patent: Sep. 11, 2018

(54) THIOUREA-CONTAINING DENDRIMER AND THIOUREA-CONTAINING HYPERBRANCHED POLYMER AS WELL AS PREPARATION METHODS THEREOF AND APPLICATIONS THEREOF

(71) Applicant: ZHEJIANG UNIVERSITY, Hangzhou, Zhejiang Province (CN)

(72) Inventors: Youqing Shen, Hangzhou (CN); Shiqun Shao, Hangzhou (CN); Jianbin Tang, Hangzhou (CN); Xiangrui Liu, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 0 days.

(21) Appl. No.: 15/516,378

(22) PCT Filed: Jan. 30, 2015

(86) PCT No.: PCT/CN2015/071874
§ 371 (c)(1),
(2) Date: Mar. 31, 2017

(87) PCT Pub. No.: WO2016/061939
PCT Pub. Date: Apr. 28, 2016

(65) Prior Publication Data
US 2017/0306101 A1   Oct. 26, 2017

(30) Foreign Application Priority Data

Oct. 21, 2014 (CN) .......................... 2014 1 0565875

(51) Int. Cl.
| | |
|---|---|
| *A61K 9/00* | (2006.01) |
| *C08G 83/00* | (2006.01) |
| *A61K 47/48* | (2006.01) |
| *C08F 228/02* | (2006.01) |
| *C08G 18/32* | (2006.01) |

(52) U.S. Cl.
CPC ...... *C08G 83/003* (2013.01); *A61K 47/48169* (2013.01); *C08F 228/02* (2013.01); *C08G 18/32* (2013.01)

(58) Field of Classification Search
CPC .................................................. C08G 83/003
See application file for complete search history.

(56) References Cited

U.S. PATENT DOCUMENTS

2013/0004427 A1*  1/2013  El-Sayed ......... A61K 47/48176
424/9.3

\* cited by examiner

*Primary Examiner* — Paul W Dickinson
(74) *Attorney, Agent, or Firm* — Jiwen Chen

(57) ABSTRACT

The present invention discloses thiourea-containing dendrimers and thiourea-containing hyperbranched polymers, and respectively a preparation method for the thiourea-containing dendrimer and a preparation method for the thiourea-containing hyperbranched polymer, and a thiourea-containing dendrimer and a thiourea-containing hyperbranched polymer having increased water solubility prepared by using the thiourea-containing dendrimer and the thiourea-containing hyperbranched polymer as raw materials. Finally, disclosed are applications of the thiourea-containing dendrimers and the thiourea-containing hyperbranched polymers in the preparation of antitumor and antimicrobial drugs. The thiourea-containing dendrimer and the thiourea-containing hyperbranched polymer have a significant growth inhibitive effect on solid tumors and low toxicity to normal tissues, and thus can be used for preparing drugs for treating malignant tumors. The thiourea-containing dendrimer and the thiourea-containing hyperbranched polymer also have a good antimicrobial effect on various bacterial strains and thus can be used for preparing antiviral or antibacterial drugs.

11 Claims, 6 Drawing Sheets

THIOUREA-CONTAINING DENDRIMER AND THIOUREA-CONTAINING HYPERBRANCHED POLYMER AS WELL AS PREPARATION METHODS THEREOF AND APPLICATIONS THEREOF

This is a U.S. national stage application of PCT Application No. PCT/CN2015/071874 under 35 U.S.C. 371, filed Jan. 30, 2015 in Chinese, claiming priority of Chinese Application No. 201410565875.6, filed Oct. 21, 2014, all of which are hereby incorporated by reference.

BACKGROUND OF THE INVENTION

The present invention relates generally to methods of polymer preparation and, more specifically, to thiourea-containing dendrimer and thiourea-containing hyperbranched polymer as well as their preparation methods and applications.

Dendrimers are a class of artificial macromolecules with tree-like topological structures, synthesized by repeated growing basic reaction with characteristic of structural perfection, and highly molecular symmetry. Generally, the synthesis methods can be classified into divergent approach (Ihre H, Padilla De Jesús O L and Fréchet J M, Fast and convenient divergent synthesis of aliphatic ester dendrimers by anhydride coupling. Journal of the American Chemical Society 2001, 123: 5908-5917.) and convergent approach (Parrott M C, Benhabbour S R, Saab C et al., Synthesis, Radiolabeling, and Bio-imaging of High-Generation Polyester Dendrimers. Journal of the American Chemical Society 2009, 131: 2906-2916.). Employing highly-efficient reactions can increase dendrimer synthesis efficiency. For instance, CN101591428B is directed to an approach to the synthesis of polyester dendrimers, wherein the method greatly simplifies the preparation and purification process by taking advantages of two Michael additions, namely thiol-methacrylate reaction and amine-acrylate reaction. In addition, using the copper(I)-catalyzed azide alkyne cycloaddition and thiol-ene addition, Craig J. Hawker et al. synthesized a class of polyester dendrimers efficiently (Antoni P, Robb M J, Campos L et al., Pushing the Limits for Thiol-Ene and CuAAC Reactions: Synthesis of a 6th Generation Dendrimer in a Single Day. Macromolecules 2010, 43: 6625-6631.). However, up to now, none of them shows inherent therapeutic efficacy.

Isothiocyanate-amine coupling is a high-efficient reaction. The resulting thiourea moiety exhibits excellent biological activities including broad spectrum antimicrobial, bactericidal and antiviral effects (Liu J, Yang S, Li X et al., Synthesis and antiviral bioactivity of chiral thioureas containing leucine and phosphonate moieties. Molecules 2010, 15: 5112-5123.). For example, CN1138323 A is directed to a water-soluble anionic polythiourea with anti-human immunodeficiency virus and anti-AIDS-related complex effect. Moreover, some thiourea-compounds exhibited antitumor activity. (Manjula S, Malleshappa Noolvi N, Vipan Parihar K et al., Synthesis and antitumor activity of optically active thiourea and their 2-aminobenzothiazole derivatives: A novel class of anticancer agents. European Journal Of Medicinal Chemistry 2009, 44:2923-2929). But these compounds were all cytotoxic agents and their antitumor activity resulted from their cell-killing behavior. For example, during in vitro experiments, these compounds all can kill cancer cells and the concentration to kill 50% of cancer cells (IC50) is at micro mole level. Such cell-killing behavior makes cytotoxic agents also harmful to normal tissues, limiting the application of such thiourea compounds.

SUMMARY OF THE INVENTION

The present invention provides thiourea-containing dendrimer and thiourea-containing hyperbranched polymer as well as their preparation methods and applications in cancer prevention and treatment. Thiourea-containing dendrimers can be facilely prepared by sequential click coupling of asymmetrical monomers; thiourea-containing hyperbranched polymers can be prepared by the one-pot reaction between monomers. Thiourea-containing dendrimers and hyperbranched polymers exhibit low cytotoxicity but dramatic tumor inhibitive effect. In addition, they also show excellent antimicrobial activity against multiple bacterial strains.

The thiourea-containing dendrimer is prepared from isothiocyanate-containing monomers ABx and amine-containing monomers CDx, In the ABx-type asymmetric monomer, the A group is an isothiocyanate group, the B group is allyl or methacrylate, x=2 to 3;

In the CDy-type asymmetric monomer, the C group is a group that reacts only with the B group, and the D group is a group that reacts only with the A group, y=1 to 3.

The A functional group, the B functional group, the C functional group and the D functional group are each different.

In the present invention, A functional group of ABx asymmetric monomer reacts only with the D functional group of CDy asymmetric reactive monomer, B functional group of ABx asymmetric monomer reacts only with C functional group of the CDy asymmetric reactive monomer. The reaction between the A functional group and the D functional group, and the reaction between B functional group and the C functional group are all click reactions.

Preferably, the monomer is an ABx-type 1-(diallylamino)-3-isothiocyanato-2-propanol or 2,2-bis(methacryloyloxymethyl)propionyl isothiocyanate, and the other is a CDy-type cysteamine monomer hydrochloride or cysteamine, wherein:

when the ABx-type monomer is 1-(diallylamino)-3-isothiocyanato-2-propanol (DA-ITC in formula I), the CDy-type monomer is cysteamine hydrochloride (CA-HCl in formula II);

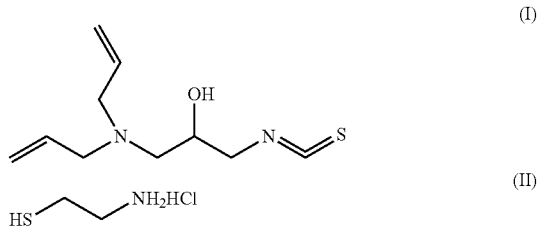

The allyl group in DA-ITC reacts with the mercapto group in CA-HCl, and the isothiocyanate group in DA-ITC reacts with the NH group after desalting in CA-HCl. The reaction mechanism of the former is free radical addition reaction, while the latter mechanism belongs to the nucleophilic addition reaction.

or when the ABx-type monomer is 2,2-bis(methacryloyloxymethyl)propionyl isothiocyanate (DMA-ITC in formula III), the CDy-type monomer is cysteamine (CA in formula IV).

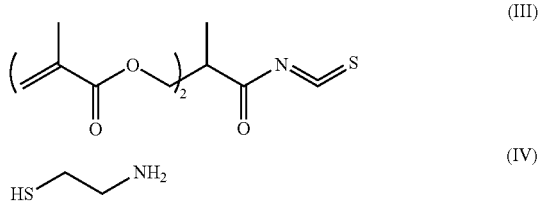

The methacryloxy groups in the DMA-ITC react with the mercapto group in CA, and the acyl isothiocyanate group in DMA-ITC reacts with the amino group in CA. The reaction mechanism of the former belongs to the typical Michael addition reaction, while the latter mechanism belongs to the nucleophilic addition reaction.

Preferably, the molecular weight of the disclosed thiourea-containing dendrimer is 100~50000.

The present invention also discloses the method of manufacture of the disclosed thiourea-containing dendrimer by sequentially stepwise reactions between the monomer pair of the ABx-type monomer and the CDy-type monomer. More specifically, the manufacture is carried out according to the procedures as following:
1) mixing a multi-amine compound with the $AB_x$-type monomer, and stirring at 0° C. under water-ice bath for 10~60 min and then at the raised temperature of ~60° C. and reacting for 2~12 hours. The first generation (G1) of the thiourea-containing dendrimer is obtained by suitable purification methods;
2) mixing the G1 dendrimer obtained in step (1) with the $CD_y$-type monomer in a suitable solvents, and reacting at room temperature for 10~60 min or under exposure to 365 nm UV-light for 1~5 hours. After purified by suitable methods, the intermediate product is obtained;
3) mixing the intermediate product obtained in step (2) with the $AB_x$-type monomer, and react at room temperature ~60° C. for 2~12 hours. The G2 thiourea-containing dendrimer is obtained by suitable purification methods;
repeating the steps (2) and (3) for n (n≥0) times can afford the G(n+2) dendrimer.

The later process comprises purification, washing and drying, etc.

Multi-amine compounds include, but are not limited to, aliphatic or aromatic diamine, triamine or multiamine with the carbon number of 2~10. The polyamine has two or more amino groups, and reacts with the isothiocyanate group in the ABx-type asymmetric monomer, resulting in a number of branched thiourea compounds, and can be used as dendritic macromolecules. Different polyamines with different structures can be used to synthesize polythiourea dendrimers with different intramolecular gaps by using the different amino groups in these polyamines. Using linear polyethyleneimines as core can afford different shapes of branches macromolecules.

Preferably, the multi-amine compounds include, but are not limited to, ethylenediamine, 1,3-diaminopropane, 1,4-diamonobutane, 1,5-diaminopentane, 1,6-diaminohexane, 1,7-diaminoheptane, 1,8-diaminooctane, 1,9-diaminononane, tris(2-aminoethyl)amine, tris(3-aminopropyl)amine, or linear polyethyleneimine of molecular weight of 100~40000.

The present invention also provides a thiourea-containing hyperbranched polymer, wherein ABx-type monomer and CDy-type monomer are dissolved in organic solvents, and exposed to ultraviolet light irradiation for 1~5 hours to obtain thiourea hyperbranched polymer;

Alternatively, reaction under room temperature ~60° C. for 2~12 hours to obtain thiourea hyperbranched polymer.

Preferably, the ABx-type monomer is 1-(diallylamino)-3-isothiocyanato-2-propanol or 2,2-bis(methacryloyloxymethyl)propionyl isothiocyanate, and the CDy-type monomer is cysteamine hydrochloride or cysteamine.

The polythiourea hyperbranched polymer has a number average molecular weight of from 300 to 100,000.

The present invention also provides a thiourea-containing dendrimer with increased water solubility. The thiourea-containing dendrimer with increased water solubility is prepared by reactions of the disclosed thiourea-containing dendrimer with hydrophilic polymers. Preferably, the hydrophilic polymers include, but are not limited to, polyethylene glycol of molecular weight of 200~2000.

The present invention also provides a thiourea-containing hyperbranched polymer with increased water solubility. The thiourea-containing hyperbranched polymer with increased water solubility is prepared by reactions of the disclosed thiourea-containing hyperbranched polymer with hydrophilic polymers. Preferably, the hydrophilic polymers include, but are not limited to, polyethylene glycol of molecular weight of 200~10,000.

The present invention also discloses the applications of the disclosed thiourea-containing dendrimer and thiourea-containing hyperbranched polymer in preparation of antitumor agents and antiviral or antibiotic drugs.

The present invention also discloses the use of said water-soluble thiourea-containing dendrimers and water-soluble polythiourea-containing hyperbranched polymers for the preparation of antineoplastic agents, antiviral or antimicrobial agents.

The disclosed thiourea-containing dendrimer and thiourea-containing hyperbranched polymer can reduce the copper level in vivo and in tumors, effectively suppress the VEGF expression and then neovascularization, leading to tumor growth inhibition finally. Under normal Cu homeostasis, copper levels are tightly regulated. However, cancer patients have aberrantly elevated serum and tumor copper levels, which is important for angiogenesis, tumorigenesis and metastasis (Ishida, S., Andreux, P., Poitry-Yamate, C., Auwerx, J. & Hanahan, D. Bioavailable copper modulates oxidative phosphorylation and growth of tumors. *Proc. Natl. Acad. Sci. USA* 110, 19507-19512 (2013)). Copper-lowering strategy is a straightforward approach to inhibiting tumor growth and metastasis (Hassouneh, B. et al. Tetrathiomolybdate promotes tumor necrosis and prevents distant metastases by suppressing angiogenesis in head and neck cancer. *Mol. Cancer Ther.* 6, 1039-1045 (2007)). The disclosed thiourea-containing dendrimer and thiourea-containing hyperbranched polymer can reduce $Cu^{2+}$ ion to $Cu^+$ ion, and form chelate (Krzewska, S., Pajdowski, L. & Podsiadly, H. Studies on the reaction of copper (II) with thiourea—II: The modification of bjerrum's method. The determination of equilibrium in simultaneous redox and complexation reactions. *J. Inorg. Nucl. Chem.* 42, 87-88 (1980)). One molecule of fifth generation thiourea-containing dendrimer can absorb massive copper ions and decrease the in vivo copper level, which inhibits angiogenesis and suppresses tumor growth and metastasis. Meanwhile, thiourea containing polymers can also decrease the level of reactive oxygen species (ROS) in tumor cells, contributing to tumor inhibition. Moreover, these thiourea-containing dendrimers or hyperbranched polymers aren't cytotoxins, so they exhibit quite low toxicity against normal cells and tissues.

Compared with currently available technology, the present invention has the following advantages:

The disclosed thiourea-containing dendrimer and thiourea-containing hyperbranched polymer show excellent bioactivity due to the presence of thiourea moieties. These polymers exhibit significant tumor inhibitive effect, specifically on human lung adenocarcinoma (A549), human breast carcinoma (BCap37), human oral epidermoid carcinoma (KB), human colorectal adenocarcinoma (SW620) and human adriamycin resistant mammary carcinoma (MCF7/ADR). Moreover, these polymers show low cytotoxicity against non-tumorigenic cell lines, including human foetal lung fibroblast (HFL1) and immortalized human bronchial epithelial (BEAS-2B) cell lines. The intraveneous administration of the polymers does not change the blood chemistry in mice. Therefore, the disclosed thiourea-containing dendrimers and thiourea-containing hyperbranched polymers have high activity of selectively inhibiting tumor growth but low toxicity to normal tissues, and can be used for the preparation of anticancer drugs.

The disclosed thiourea-containing dendrimer and thiourea-containing hyperbranched polymer have excellent antimicrobial and bactericidal effects on multiple bacterial strains including *Staphylococcus aureus* (*S. aureus*), *Enterococcus faecalis* (*E. faecalis*), *Escherichia coli* (*E. coli*), *Staphylococcus epidermidis* (*S. epidermidis*), *Enterobacter cloacae* (*E. cloacae*) and *Proteus valgaris* (*P. valgaris*), and can be used for the preparation of antimicrobial drugs.

The disclosed thiourea-containing dendrimers and thiourea-containing hyperbranched polymers have low toxicity to normal tissues, and can be used as biomaterial, specifically as drug delivery carrier; the massive terminal groups can be used to conjugate with different therapeutic agents, imaging agents or targeting groups, facilitating the development of drug delivery system.

EXAMPLES

Figure 1:
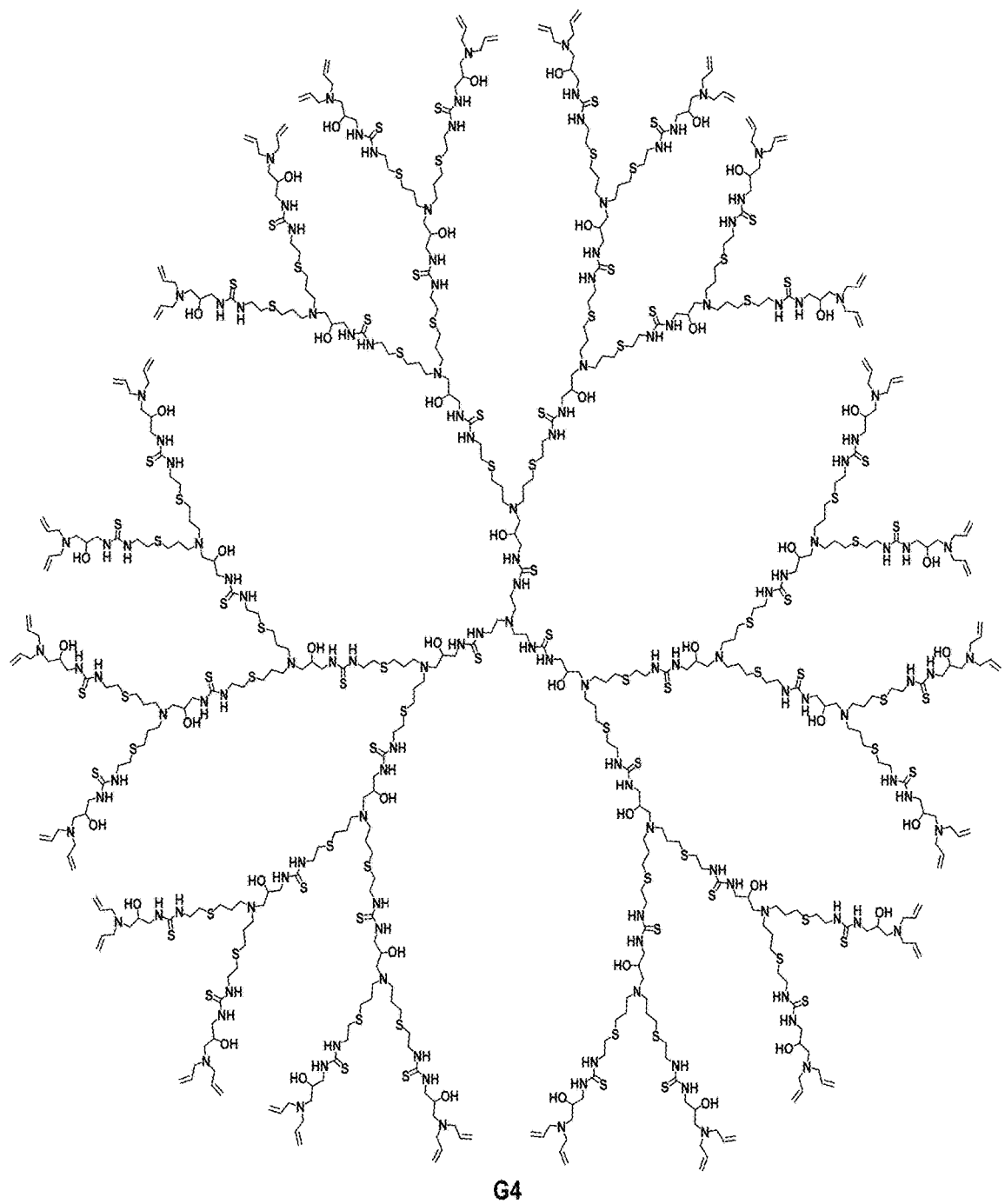
FIG. 1 shows the synthetic route of the fourth generation (G4) thiourea-containing dendrimer as described in Example 1.
Figure 2:
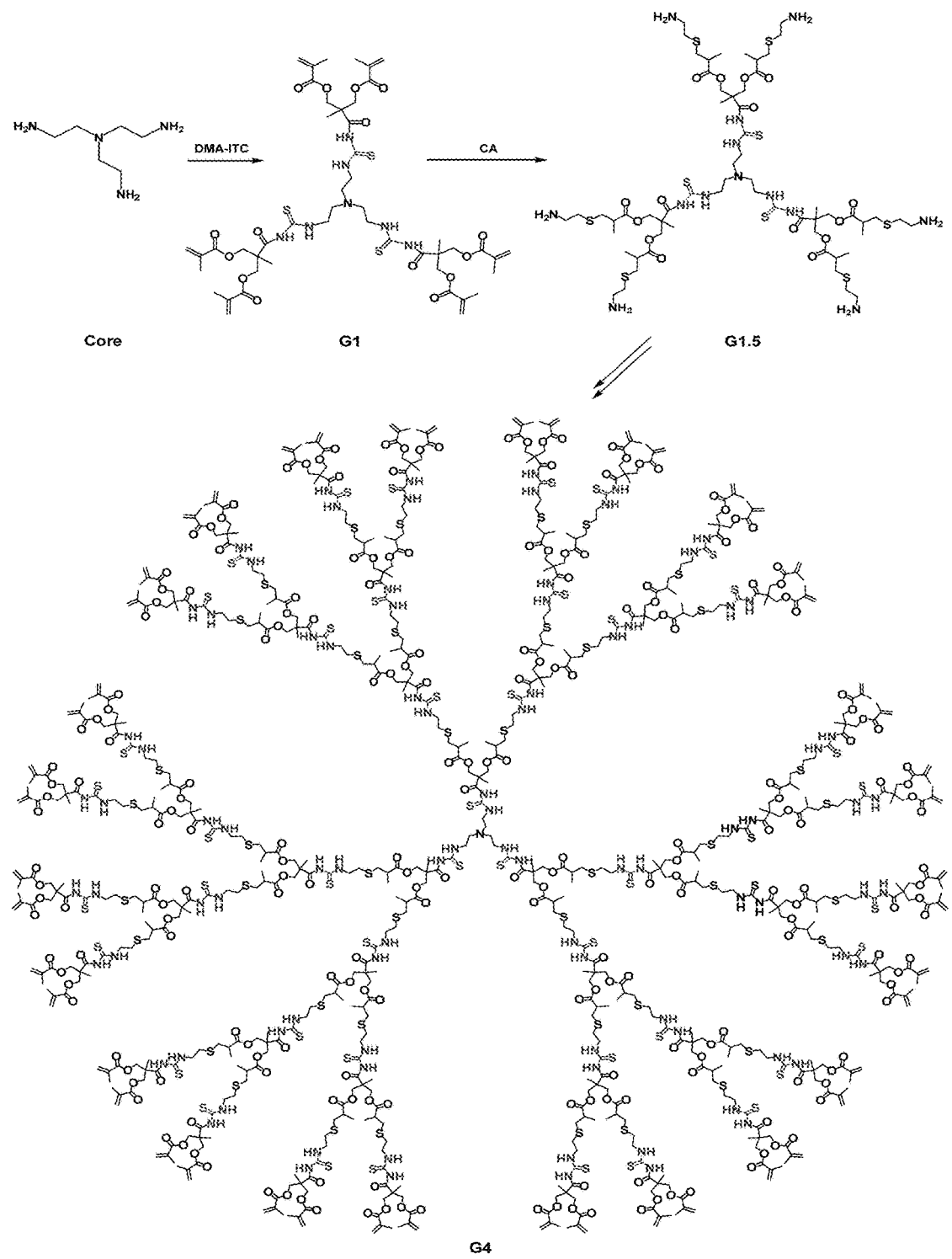
FIG. 2 shows the synthetic route of G4 thiourea-containing dendrimer as described in Example 2.

Example 1—Synthesis of Thiourea-Containing Dendrimers from a Monomer Pair of 1-(diallylamino)-3-isothiocyanato-2-propanol (DA-ITC) and cysteamine hydrochloride (CA-HCl) with tris(2-ethylamino)amine as the Core 1) Synthesis of the AB$_x$-Type Monomer 1-(diallylamino)-3-isothiocyanato-2-propanol (DA-ITC)

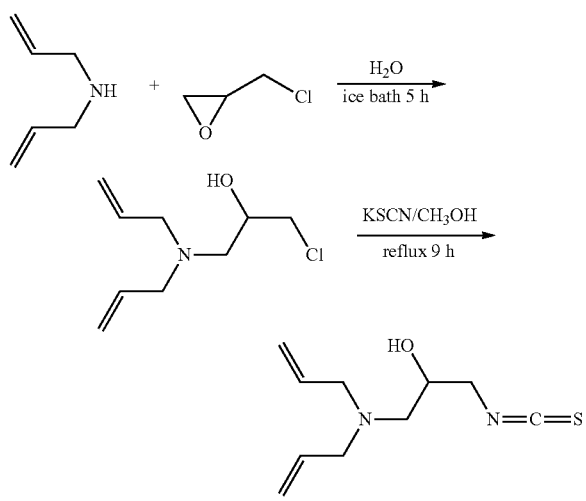

Diallylamine (24.3 g, 0.25 mol), epichlorohydrin (25.0 g, 0.27 mol) and deion water (25 mL) were combined at 0° C. for 5 hours. The resulting reaction mixture was extracted with CH$_2$Cl$_2$ (60 mL×3). The organic phase was dried with anhydrous MgSO$_4$. The solvent and an excess epichlorohydrin were removed under high vacuum. The resulting colorless oil was re-dissolved in 150 mL of anhydrous methanol, adding potassium thiocyanate (29.2 g, 0.30 mol). The mixture was refluxed for 9 hours. The precipitate was filtered and the filtrate was concentrated. The resulting mixture was re-dissolved in 150 mL CH$_2$Cl$_2$ and washed with water (100 mL×3). The organic phase was dried with anhydrous MgSO$_4$ and then the solvent was evaporated. The pure product was obtained by distillation under reduced pressure as a colorless oil with an 80% yield.

2) Synthesis of the First Generation of Thiourea-Containing Dendrimer (A-G1)

Tris(2-aminoethyl)amine (1.15 g, 7.88 mmol) and DA-ITC (5.65 g, 26.21 mmol) were combined at 0° C. for 15 min, then heated at 60° C. overnight. The product was obtained by distillation of excess of DA-ITC as a colorless oil with a yield of 99%.

3) Synthesis of the Amine-Terminated Thiourea-Containing Dendrimer (A-G1.5)

A-G1 (0.5 g, 0.64 mmol), CA-HCl (4.4 g, 38.72 mmol), and 2,2-dimethoxy-2-phenylacetophenone (0.20 g, 0.78 mmol) were added into a vessel. Methanol (5 mL) was added as a solvent and the mixture was sparged with dried nitrogen for 15 min and then exposed to the 365 nm UV-lamp for 2 hours at room temperature. Triethylamine (10 mL) was added into the resulting reaction mixture and stirred for about 30 min. Methanol and excess triethylamine were evaporated and then deionized water (5 mL) were added. The resulting mixture was washed with diethyl ether (20 mL×3). After dialysis against deionized water, the solution was freeze-dried to obtained pure product A-G1.5 with a yield of 46%.

4) Synthesis of the Second Generation of Thiourea-Containing Dendrimer (A-G2)

A-G1.5 was dissolved in MeOH. A small excess of DA-ITC was then added dropwise and the mixture was stirred at room temperature for 15 min, and then heated at 55° C. overnight. The pure product was obtained by precipitation in ether (50 mL×3) with a yield of 93%.

5) Synthesis of the Fourth Generation of Thiourea-Containing Dendrimer (A-G4)

A-G2.5 was synthesized according to the procedure of synthesizing amino-functional polythiourea dendrimer A-G1.5, and then the A-G2.5 was synthesized according to the step of synthesizing polythiourea dendrimer A-G2 A-G3. Repeating the above steps (3) and (4) sequentially twice can afford the fourth generation of thiourea-containing dendrimer (A-G4).

Example 2—Synthesis of Thiourea-Containing Dendrimers from a Monomer Pair of 2,2-bis(methacryloyloxymethyl)propionyl isothiocyanate (DMA-ITC) and cysteamine (CA) with tris(2-ethylamino) amine as the Core 1) Synthesis of 2,2-bis(methacryloyloxymethyl)propionyl isothiocyanate (DMA-ITC)

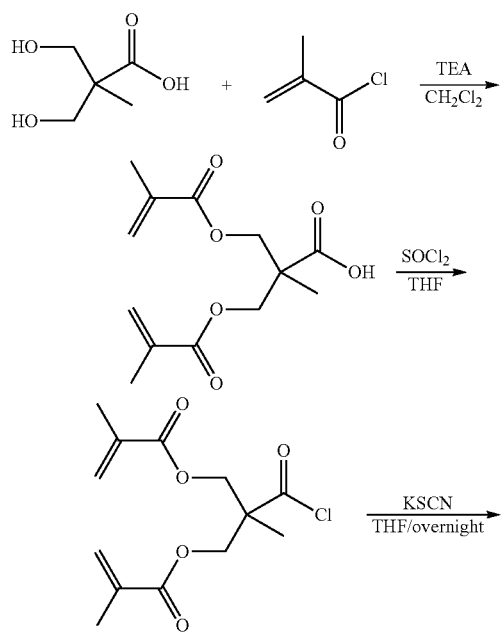

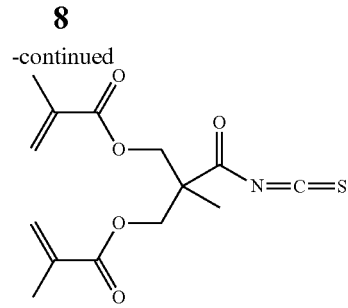

2,2-Bis(methacryloyloxymethyl)propionate acid (5.0 g, 18.5 mmol) was dissolved in 50 mL of dry THF. Thionyl chloride (6 mL, 84.2 mmol) was added to the solution and heated to reflux for 3 hours. The solvent and excess thionyl chloride were removed under vacuum. The product was dissolved in 30 mL of dry THF and dry KSCN (2.65 g, 27.2 mmol) was added to the solution. The reaction mixture was stirred overnight at room temperature. The resulting mixture was filtered and the filtrate was purified by column chromatography to obtain DMA-ITC as a colorless liquid.

2) Synthesis of the First Generation of Thiourea-Containing Dendrimer (M-G1)

Tris(2-aminoethyl)amine (0.50 g, 3.35 mmol) in 5 mL dry DCM was cooled to 0° C. in ice bath. DMA-ITC (3.86 g, 12.41 mmol) was added dropwise to the solution. The solution was stirred at room temperature for 3 hours. The pure product was obtained by reprecipitation in hexane (50 mL×3) as a colorless oil M-G1 with a 95% yield.

3) Synthesis of the Second Generation of Thiourea-Containing Dendrimer (M-G2)

The obtained M-G1 dendrimer (0.51 g, 0.47 mmol) and CA (0.30 g, 4 mmol) were dissolved in 4 mL anhydrous DMSO and stirred at room temperature for 30 min. DCM (50 mL) was then added to dilute the solution followed by washing with cold brine (100 mL×3). The organic phase was dried with anhydrous magnesium sulfate. After concentration, DMA-ITC (1.1 times extra amount) was added dropwise to the solution. After stirred at room temperature for 4 hours, the M-G2 dendrimer was obtained by precipitation in ether as a colorless oil with a 90% yield.

4) Synthesis of the Fourth Generation of Thiourea-Containing Dendrimer (M-G4)

Following the step of synthesizing the second-generation polythiourea dendrimer M-G2, M-G3 is synthesized and the above-mentioned step is repeated to obtain the fourth generation of thiourea-containing dendrimer (M-G4).

Example 3—PEGylation of the Thiourea-Containing Dendrimer

The M-G4 dendrimer (0.5 g) and PEG550-SH (2 g) were dissolved in 2 mL DMSO. Three drops of Bu₃P were added to the solution. The solution was stirred at room temperature overnight and then poured into ether. The precipitate was isolated and purified by reprecipitation (50 mL×3). Finally, the product M-G4-PEG was obtained as a colorless oil (1.1 g).

The PEGylated low-generation dendrimers (i.e., M-G1-PEG, M-G2-PEG and M-G3-PEG) were synthesized following the procedure used for the synthesis of M-G4-PEG.

Example 4—Synthesis of Thiourea-Containing Hyperbranched Polymer via the Reaction of 2,2-bis(methacryloyloxymethyl)propionyl isothiocyanate (DMA-ITC) and cysteamine (CA)

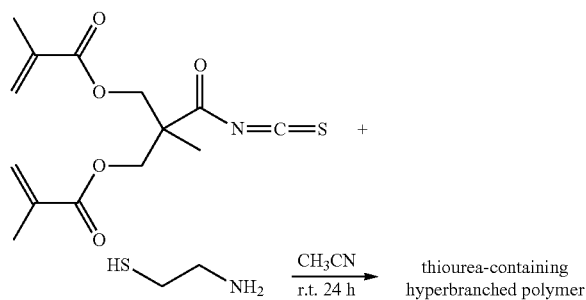

DMA-ITC (1.24 g, 4 mmol) and CA (0.31 g, 4 mmol) were dissolved in 50 mL of $CH_3CN$, and stirred at r.t. for 24 h. The thiourea-containing hyperbranched polymer was obtained by precipitation in ether as a colorless syrup with a 92% yield.

The hyperbranched polymer (0.5 g) and PEG550-SH (2 g) were dissolved in 2 mL DMSO. Three drops of $Bu_3P$ were added to the solution. The solution was stirred at room temperature overnight and then poured into ether. The precipitate was isolated and purified by reprecipitation. Finally, the product M-HB-PEG was obtained as a colorless syrup (1.1 g).

Performance Testing:

I. Formation of the M-G4-PEG/Cu Complex

Figure 3:
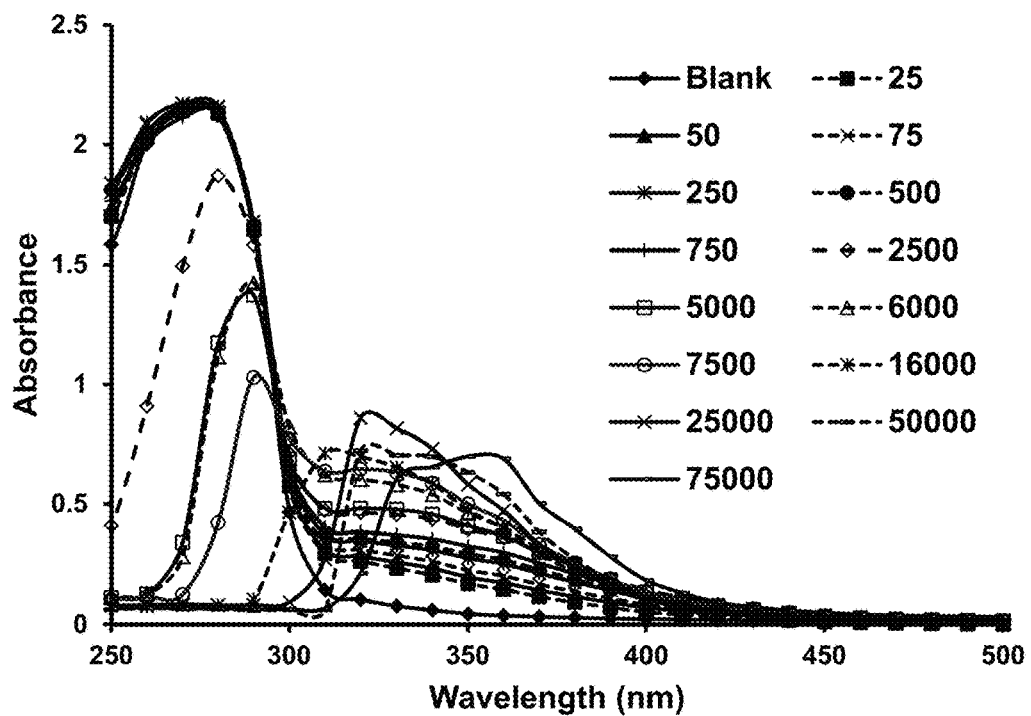
FIG. 3 shows the complexion of the PEGylated G4 thiourea-containing dendrimer (M-G4-PEG) with copper ions as described in Example 3; the number shown in the figure refers to the molar ratio of Cu(II) ions to M-G4-PEG.

In brief, UV-Vis spectra of M-G4-PEG (10 μM) solution was added with different amounts of $CuCl_2$ (Cu/dendrimer molar ratios) were recorded from 250 nm~500 nm. Each M-G4-PEG/$CuCl_2$ solution was filtered through an Amicon® Ultra-4 3K device. The ultrafiltration filtrate was collected and its UV-Vis spectrum, i.e., spectrum of uncomplexed $CuCl_2$ in the solution, was recorded under the exactly same conditions as above. The UV-Vis spectrum of M-G4-PEG/Cu complex formed at each Cu/dendrimer molar ratio was obtained by subtracting the spectrum of uncomplexed $CuCl_2$ from those of the original solution. The intensities at 270 nm (M-G4-PEG) and 350 nm (M-G4-PEG/Cu complex) were plotted against the Cu/M-G4-PEG molar ratio. As shown in FIG. 3, upon addition of Cu(II) ions into the M-G4-PEG aqueous solution, the absorption peak at 270 nm of acylthioureas shifted gradually and disappeared at high Cu(II) concentrations, while a plateau at approximately 320-350 nm appeared. The binding number (n) and the degree of dissociation of complex (a) were estimated by extrapolation method. The stability constant (K) for the formation of dendrimer/Cu complex was calculated using the following formula:

$$\log K = \log(1-a) - (n+1)\log a - n \log C - n \log n,$$

where C was the molar concetration of M-G4-PEG in the solution. The binding constant and binding number were determined to be $10^{26873}$ $(mol/L)^{-16000}$.

II. In Vitro Assay

1. In Vitro Cytotoxicity Assay

The cytotoxicity of M-G4-PEG to cell lines, including human lung adenocarcinoma (A549), human breast carcinoma (BCap37), human oral epidermoid carcinoma (KB), human colorectal adenocarcinoma (SW620) and human adriamycin resistant mammary carcinoma (MCF7/ADR), human foetal lung fibroblast (HFL1) and immortalized human bronchial epithelial (BEAS-2B) cell lines, was determined by 3-(4,5-dimethylthiazol-2-yl)-2,5-diphenyltetrazolium bromide (MTT) cell-proliferation assay.

The detection principle of the MTT method is that the succinate dehydrogenase in the mitochondria of the living cells can reduce the exogenous MTT into water-insoluble blue-violet crystalline formazan and deposit it in the cells, while the dead cells do not have this function. DMSO can dissolve cells in the formazan, with enzyme-linked immunosorbent assay to determine the light absorption value, can indirectly reflect the number of living cells. Within a certain number of cells, the amount of MTT crystals formed is proportional to the number of cells.

Figure 4:
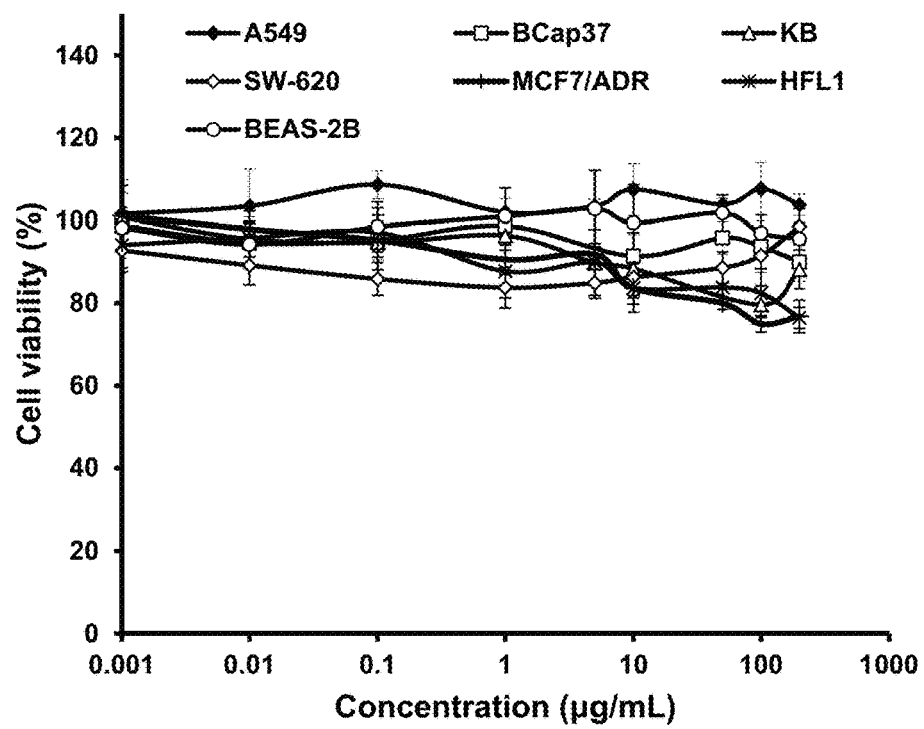
FIG. 4 shows the cytotoxicity of the PEGylated G4 thiourea-containing dendrimer (M-G4-PEG) to human tumor cell lines and human normal cell lines as described in Example 3.

Exemplified by PEGylated fourth-generation polythiourea dendrimer (M-G4-PEG) prepared in Example 2 and BCap37 cells, BCap37 cells were trypsinized with 0.25% trypsin, and then diluted to $4.5 \times 10^7$ cell/L with RPMI-1640 medium containing 10% fetal bovine serum, 100 U/mL penicillin and streptomycin. Then the cells were inoculated in 96-well plate. After 24 hours of culture, the medium was replaced, and each well was added with different concentrations of M-G4-PEG. After 48 hours of dosing, 100 μL of RPMI-1640 medium containing MTT was added and incubated for 3 hours. After centrifugation, the supernatant was removed and 100 μL of DMSO was added to each well and mixed by shaking. The absorbance (A) of each well was measured when the wavelength was 562 nm and the reference wavelength was 620 nm. Cell viability was calculated according to the following formula:

Cell survival rate=(experimental group $A$ value/blank group $A$ value)×100%;

As shown in FIG. 4, M-G4-PEG is non-cytotoxic to various human tumor cell lines (A549, BCap37, KB, SW620 and MCF7/ADR) and non-tumorigenic cell lines (HFL1 and BEAS-2B). As shown in FIG. 4, M-G4-PEG had no cytotoxicity to the above cells. This indicates that the polythiourea dendrimer is completely safe and non-toxic. After injected into the body, even if the molecules in the circulation diffuses into other normal tissues, it will not cause damage to normal tissues.

2. In Vitro ROS Detection

2',7'-dichlorofluorescin diacetate ($H_2DCF$-DA) was used to determine the effects of M-G4-PEG and M-HB-PEG on the intracellular ROS level. After incubation overnight, each well was added with blank medium, blank medium, M-G4-PEG (4 μM) or M-HB-PEG (4 μM). After treated for 6 hours, cells were trypsinizd with 0.1% trypsin, washed twice with PBS, resuspended in PBS and then added with 10 μM of $H_2DCF$-DA. After incubated with the respective dyes at 37° C. for 30 min, the cells were carefully washed 3 times with PBS and the fluorescence values were analyzed by flow cytometry.

Figure 5:
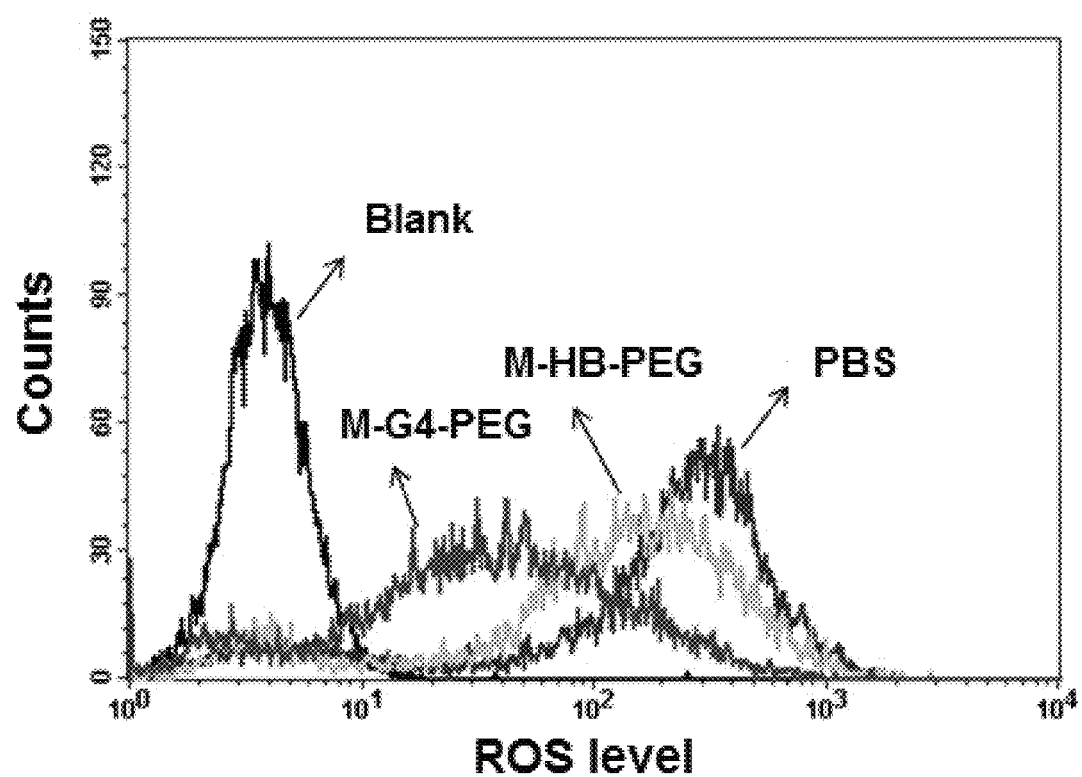
FIG. 5 shows the effects on the cellular ROS levels after incubated with the PEGylated G4 thiourea-containing dendrimer (M-G4-PEG) as described in Example 3 and the PEGylated thiourea-containing hyperbranched polymer (M-HB-PEG) as described in Example 4.

FIG. 5 shows that both M-G4-PEG and M-HB-PEG can decrease the intracellular ROS level in BCap37 cells. As shown in FIG. 5, both M-G4-PEG and M-HB-PEG can decrease intracellular ROS levels and M-G4-PEG has lower ROS than M-HB-PEG.

III. In Vivo Test

1. The Body Copper Lowering Experiment

The in vivo copper-lowering activity of M-G4-PEG and M-HB-PEG in terms of serum ceruloplasmin activity was tested. Mice (n=3/group) were i.v. injected with either M-G4-PEG (6 mg thiourea/kg) or M-HB-PEG (6 mg thiourea/kg). Blood samples were collected from the retrobulbar erties of the PEGylated polythiourea dendrimers prepared in Example 3 influences. According to the analysis of variance, there was no significant difference between the biochemical indexes of the mice treated with PEGylated thioglycan dendrimers and the blank control group, indicating that the PEGylated polythiourea dendrimers do not affect the normal tissues of mice and have no organ toxicity to mice.

TABLE 1

| ICR mice | PBS | M-G1-PEG | M-G2-PEG | M-G3-PEG | M-G4-PEG | ANOVA P-levels[†] |
|---|---|---|---|---|---|---|
| ALT (U/L) | 48.67 ± 2.52 | 50.33 ± 3.06 | 49.33 ± 3.79 | 48.50 ± 3.59 | 47.96 ± 2.51 | >0.82 |
| CK (U/L) | 626.3 ± 105.63 | 884.0 ± 63.93 | 820.67 ± 142.89 | 734 ± 103.23 | 747 ± 54.89 | >0.06 |
| CKMB (U/L) | 449.3 ± 93.01 | 620.3 ± 53.52 | 582.67 ± 122.02 | 548.33 ± 73.08 | 570.33 ± 114.64 | >0.14 |
| AST (U/L) | 80 ± 4 | 88.33 ± 6.35 | 90.67 ± 9.07 | 82.67 ± 4.35 | 87.33 ± 6.23 | >0.21 |
| LDH (U/L) | 460.67 ± 31.01 | 409 ± 90.95 | 350.33 ± 38.48 | 370.67 ± 35.54 | 420.67 ± 40.78 | >0.15 |
| UREA (U/L) | 7.54 ± 0.84 | 7.28 ± 1.27 | 7.38 ± 0.42 | 7.32 ± 0.76 | 7.50 ± 0.54 | >0.94 |
| CREA (U/L) | 21.79 ± 4.17 | 16.16 ± 1.57 | 17.45 ± 2.09 | 20.12 ± 2.01 | 19.87 ± 2.05 | >0.11 |

ALT, alanine transaminase; CK, creatine kinase; CKMB, creatine kinase mb isoenzyme; AST, aspartate transaminase; LDH, lactate dehydrogenase; UREA, blood urea nitrogen; CREA, creatinine; ANOVA, analysis of variance.
[†]All Turkey post hoc comparison, P-levels > 0.05.

venous plexus of mice 6 hours post injection. Blood samples were centrifuged at 7200 rpm for 2 min (4° C.) to obtain serum.

Two tubes each containing 50 μL mouse serum and 750 μL of 0.1 M sodium acetate buffer (pH 5.0) were incubated for 5 min in a 30° C. water bath. Prewarmed 200 μL o-dianisidine dihydrochloride solution (2.5 g/L) was then added into each tube, starting the timer at the first substrate addition. The reaction was allowed to continue for exactly 30 min in one tube and exactly 45 min in the other. Finally, the reaction was terminated by adding 2 mL of 9 M sulfuric acid. The absorbance of both tubes was measured at 540 nm using a Molecular Devices microplate reader. Ceruloplasmin concentration in IU was calculated using the formula:

$$\text{Ceruloplasmin oxidase activity} = (A_{45} - A_{30}) \times 0.625 \text{ U/mL},$$

wherein $A_{45}$ and $A_{30}$ are the absorbance at 45 and 30 min, respectively.

Figure 6:
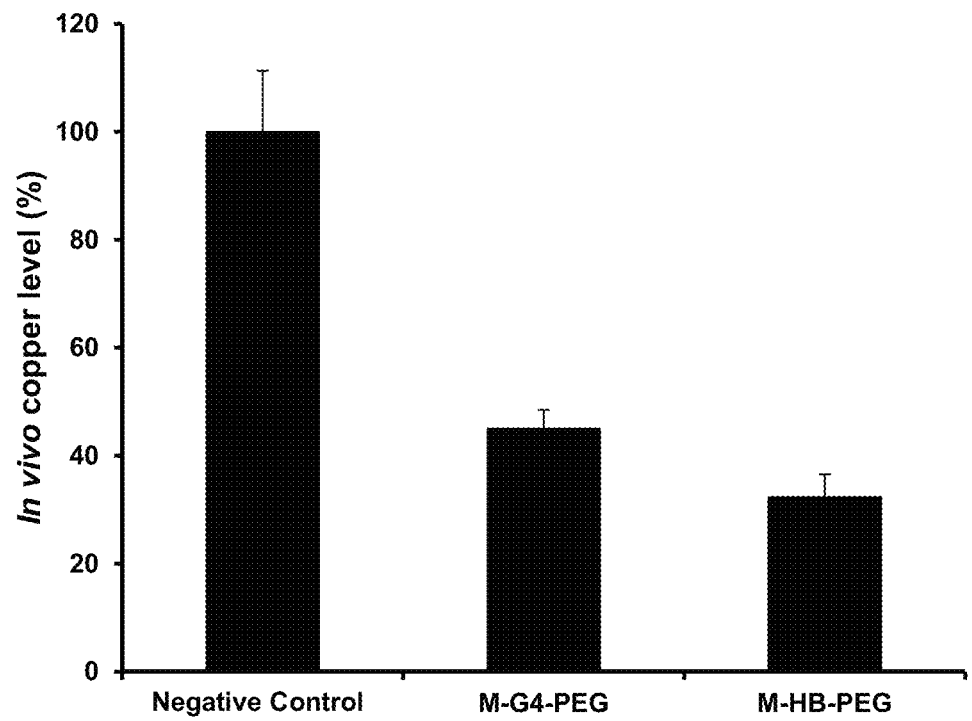
FIG. 6 shows the in vivo copper-lowering profiles of mice at 6 hours after the intraveneous administration of the PEGylated G4 thiourea-containing dendrimer (M-G4-PEG) as described in Example 3 and the PEGylated thiourea-containing hyperbranched polymer (M-HB-PEG) as described in Example 4.

FIG. 6 shows that both M-G4-PEG and M-HB-PEG can effectively decrease the in vivo copper level of mice.

2. In Vivo Tumor Inhibition Test

Figure 7:
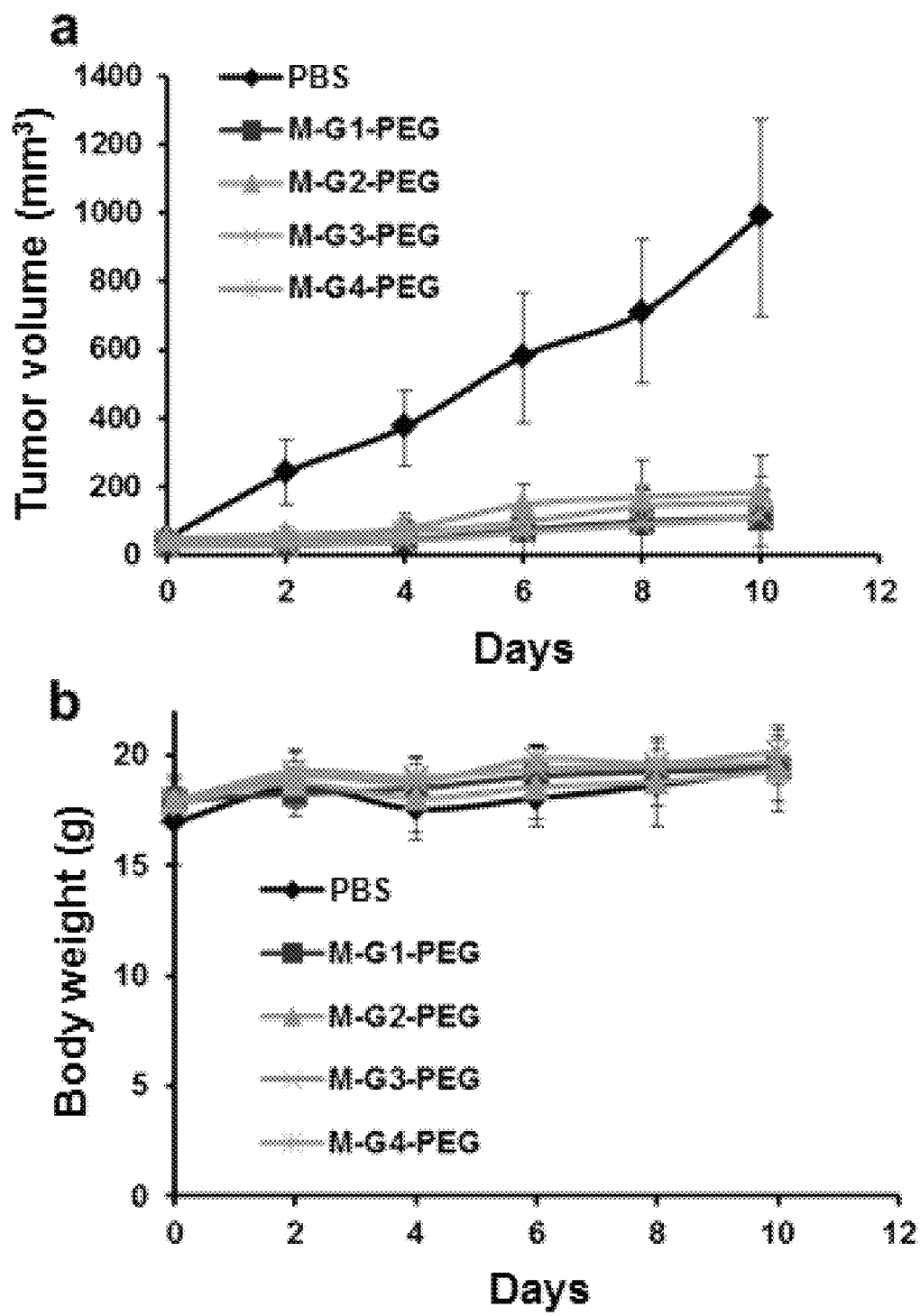
FIG. 7 shows the inhibitive effect of the PEGylated thiourea-containing dendrimer (M-G1-PEG, M-G2-PEG, M-G3-PEG and M-G4-PEG) as described in Example 3 on the growth of human colorectal cancer model in nude mice.

ICR mice (n=7/group) were i.v. injected with PBS as a control or different generations of PEGylated thiourea-containing dendrimer (0.05 mmol of thiourea/kg) daily for 5 days. Blood samples were collected for serum chemistry analysis one day after the 5th injection. The size of the nude mice and the weight of the nude mice were recorded before each administration. The specific results were shown in FIGS. 7a and 7b, respectively. Where the tumor volume is calculated as follows:

$$\text{Tumor volume} = \text{length} \times \text{width} \times \text{width}/2;$$

The mice were subject to an intradermal toxicity test in vivo with the pegylated thiourea dendrimers synthesized in Example 3, and the control and experimental groups were set up in each group of 7 mice at a dose of 0.05 mmol thiourea-eq./kg. Administration was carried out for 5 times. After the end of the administration, the mouse blood was collected from the retrobulbar venous plexus of mice, and centrifuged at 7200 rpm for 2 minutes. Serum was collected and serum biochemical tests were performed.

Table 1 below shows the effects of M-G1-PEG, M-G2-PEG, M-G3-PEG and M-G4-PEG on the biochemical prop- An ideal anticancer drug should not only be able to efficiently suppress tumor growth but also have no cytotoxicity or be specifically toxic to only tumor cells. Considering that the polythiourea dendrimers have no cytotoxicity to normal cells or tumor cells but exhibit excellent tumor inhibitive activity, the polythiourea dendrimers disclosed in the present invention have great potential as anticancer drugs.

Figure 8:
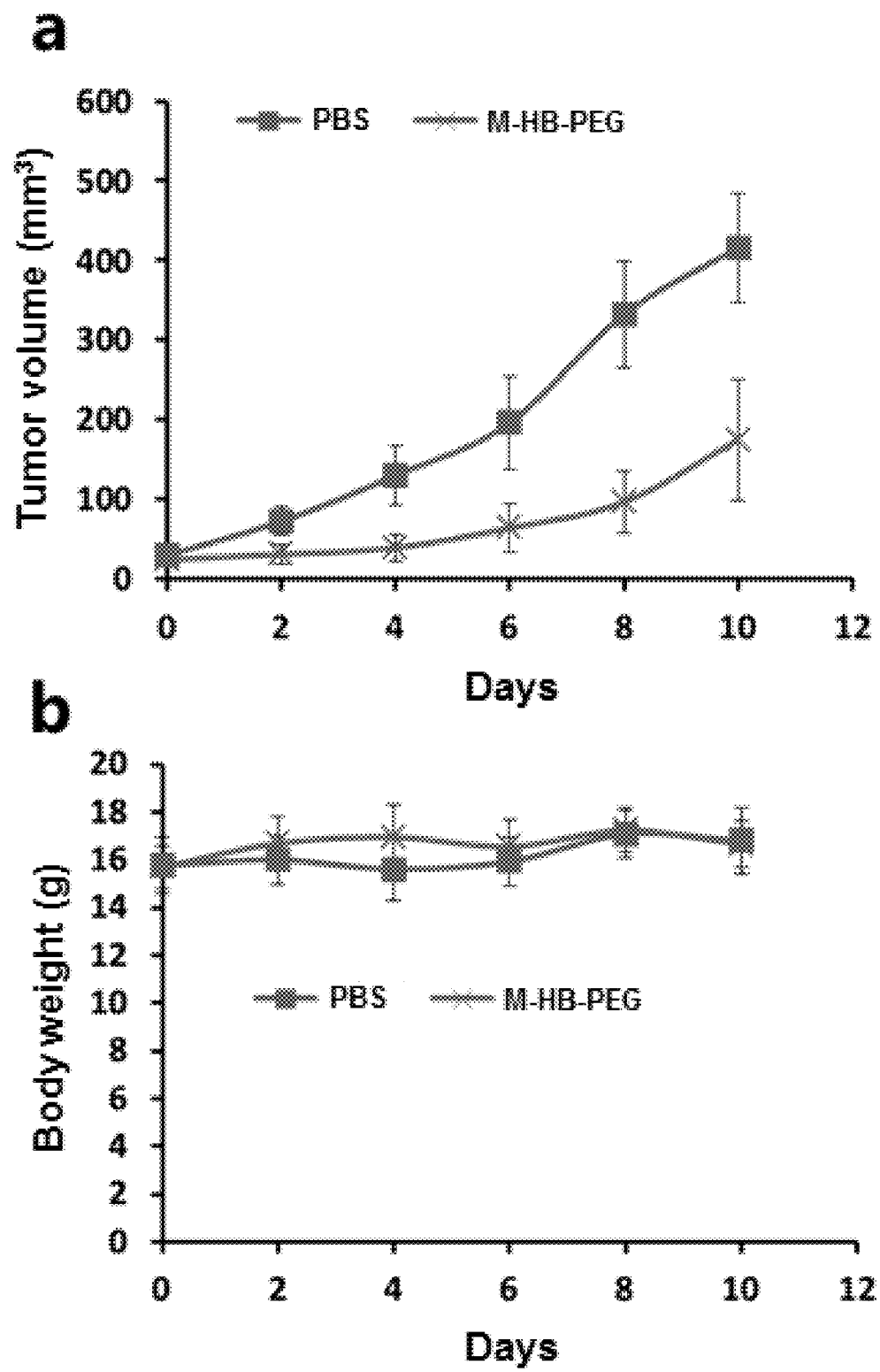
FIG. 8 shows the inhibition effect of the PEGylated thiourea-containing hyperbranched polymer (M-HB-PEG) as described in Example 4 on the growth of human colorectal cancer model in nude mice.

The human colorectal cancer tumor model of nude mice was subject to an in vivo tumor inhibition of thiourea-containing hyperbranched polymer. Tumor-bearing nude mice (n=7/group) were i.v. injected with PBS as a control or PEGylated thiourea-containing hyperbranched polymer (50 mg/kg) every other day for 5 times. Prior to each administration, the sizes of the tumors and the body weights of mice were measured. The results are shown in FIG. 8a and FIG. 8b. As shown in FIG. 8a, treatment with the thiourea-containing hyperbranched polymer can effectively inhibit tumor growth. FIG. 8b shows that the thiourea-containing hyperbranched polymer has no systemic toxicity to nude mice.

IV. Antibacterial Performance Test

To evaluate the antimicrobial activity of each generation of polythiourea dendrimer as described in Example 3, the MICs (minimal inhibitory concentrations) of these dendrimers against different bacteria strains, including *Staphylococcus aureus*, *Enterococcus faecalis*, *Escherichia coli*, *Staphylococcus epidermidis*, *Enterobacter cloacae* and *Proteus valgaris* were determined.

The strains stored at −20° C. were inoculated on MH agar plates and incubated overnight at 37° C. The monoclonal colonies were cultured in 3 mL nutrient broth at 37° C. to reach the logarithmic growth period. Then the bacteria were diluted with the MH broth to 0.5 millet turbidity standard and further diluted to 1:100 with MH broth as a stock. The diluted bacteria should be inoculated within 15 min. The polythiourea dendrimers were diluted with sterile water into 200 mg/mL, filtered and sterilized. Gentamicin and amikacin were used as positive controls for Gram-negative and Gram-positive bacteria, respectively. Dispense 100 μL of M-H broth into all wells of 96-well plate, and then pipette 100 μL of M-G1-PEG, M-G2-PEG, M-G3-PEG, M-G4-PEG, antibiotics and MH broth in the first column in the order of labeling. After mixing well with the gun, transfer 100 μL from each well in the first column to the corresponding well in the second column. Repeat the procedure to column 10 and discard 1004, from column 10. Then 100 μL of bacteria was added to each well. The final bacterial solution concentration per well was $5\times10^5$ CFU/mL. On the outer periphery of the 96-well plate, 200 μL of the drug-free suspension was added as a sterile control. At the same time subculture the suspension in the agar plate, for assessing the purity of bacteria. The inoculated 96-well plates were shaken on a micro-shaker for 1 min, mixed thoroughly and placed in a wet box. After incubated for 24 h at 37° C., the minimum drug concentration of the clear well was observed by the naked eye as the MIC of the drug. At the same time, it was examined whether the growth of the control well was good and the sterile control well was clear. The plate culture of the suspension was examined to determine whether it was contaminated and whether the MIC value of the control strain was in the control range. This assay was repeated three times.

| Antibiotic | E. cloacae | E. coli | P. valgaris | S. epidermidis | E. faecalis | S. aureus |
|---|---|---|---|---|---|---|
| M-G1-PEG | 80 | 80 | 80 | 80 | 80 | 80 |
| M-G2-PEG | 80 | 80 | 50 | 50 | 50 | 50 |
| M-G3-PEG | 10 | 10 | 10 | 25 | 30 | 20 |
| M-G4-PEG | 10 | 10 | 10 | 25 | 20 | 20 |
| PC* | 2** | 1** | 2** | 0.5*** | 4*** | 2*** |

*Positive control;
**Gentamicin;
***Amikacin

The M-G1-PEG, M-G2-PEG, M-G3-PEG and M-G4-PEG of the PEGylated thiourea-containing dendrimers prepared in Example 3 for the common Gram-negative bacteria and Gram-positive bacteria minimum inhibitory concentration. As shown in Table 2, each PEGylated thiourea-containing dendrimers can better inhibit the growth of bacteria, with MIC values of 25~200 μg/mL. Moreover, these dendrimers have higher antibiotic effect against Gram-positive bacteria than against Gram-negative bacteria.

The invention claimed is:

1. A thiourea-containing dendrimer characterized in that it is prepared by reacting an ABx-type monomer containing isothiocyanates and a CDy-type monomer containing amino groups, wherein said ABx-type monomer is 1-(2-hydroxy-3-diallylamino) propyl isothiocyanate or 2,2-bis (methacryloyloxymethyl) propionyl isothiocyanate, and the CDy-type monomer is cysteamine hydrochloride or cysteamine.

2. The thiourea-containing dendrimer according to claim 1, wherein the thiourea-containing dendrimer has a number average molecular weight of 100 to 50000.

3. A method for producing a thiourea-containing dendrimer claim 1, wherein the ABx-type monomer and the CDy-type monomer are prepared by stepwise reaction to obtain the thiourea-containing dendrimer, comprising the following steps:
    (1) mixing polyamine with the ABx-type asymmetric monomer in an ice-water bath, stirring for 10 to 60 minutes, and then raising the temperature to from room temperature to about 60° C. for 2 to 12 hours, and then after further processing to obtain polythiourea dendrimers of a first generation;
    (2) mixing the polythiourea dendrimers of the first generation obtained from the step (1), the CDy-type asymmetric monomer and a solvent, reacting under room temperature for 10 to 60 minutes or under ultraviolet radiation for 1 to 5 hours, and then after further processing to obtain an intermediate product;
    (3) mixing the intermediate product obtained in step (2) with ABx-type asymmetric monomer, and the reaction is carried out at from room temperature to about 60° C., to obtain polythiourea dendrimers of a second generation;
    repeating steps (2)-(3) 1 to N times, respectively, to prepare polythiourea dendrimers of a third generation to (N+2)th generation.

4. The method for producing a thiourea-containing dendrimer according to claim 3, wherein the polyamine is ethylenediamine, 1,3-propanediamine, 1,4-butanediamine, 1,5-pentanediamine, 1,6-hexanediamine, 1,7-heptanediamine, 1,8-octanediamine, 1,9-nonanediamine, tris (2-aminoethyl) amine, tris (3-aminopropyl) amine or linear polyethyleneimine having a number average molecular weight of 100 to 40,000.

5. A thiourea-containing hyperbranched polymer characterized in that ABx-type monomers and CDy-type monomers are dissolved in an organic solvent and radiated by ultraviolet light for 1 to 5 hours or at from room temperature to about 60° C. for 2 to 12 hours, to obtain a thiourea-containing hyperbranched polymer, wherein said ABx-type monomer is 1-(2-hydroxy-3-diallylamino) propyl isothiocyanate or 2,2-bis (methacryloyloxymethyl) propionyl isothiocyanate, and the CDy-type monomer is cysteamine hydrochloride or cysteamine.

6. A thiourea-containing dendrimer with increased water solubility characterized in that it is obtained by reacting a dendrimer containing thiourea with a hydrophilic polymer, said hydrophilic polymer having a number average molecular weight of 200~10,000 polyethylene glycol, wherein said ABx-type monomer is 1-(2-hydroxy-3-diallylamino) propyl isothiocyanate or 2,2-bis (methacryloyloxymethyl) propionyl isothiocyanate, and the CDy-type monomer is cysteamine hydrochloride or cysteamine.

7. A thiourea-containing hyperbranched polymer with increased water solubility characterized in that it is obtained by reacting a thiourea-containing hyperbranched polymer with a hydrophilic polymer having a number average molecular weight of 200~10,000 polyethylene glycol, wherein said ABx-type monomer is 1-(2-hydroxy-3-diallylamino) propyl isothiocyanate or 2,2-bis (methacryloyloxymethyl) propionyl isothiocyanate, and the CDy-type monomer is cysteamine hydrochloride or cysteamine.

8. A method of preparing antitumor drugs, antiviral or antimicrobial agents comprising the step of utilizing the thiourea-containing dendrimers according to claim 1.

9. A method of preparing antitumor drugs, antiviral or antimicrobial agents comprising the step of utilizing the water-soluble increased thiourea-containing dendrimer according to claim 6.

10. A method of preparing antitumor drugs, antiviral or antimicrobial agents comprising the step of utilizing the thiourea-containing hyperbranched polymers according to claim 5.

11. A method of preparing antitumor drugs, antiviral or antimicrobial agents comprising the step of utilizing the water-soluble increased thiourea-containing hyperbranched polymer according to claim 7.

* * * * *